(12) United States Patent
Stelkes-Ritter et al.

(10) Patent No.: US 6,333,176 B1
(45) Date of Patent: Dec. 25, 2001

(54) PROCESS FOR OBTAINING MICROORGANISMS CONTAINING PEPTIDE AMIDASE, MICROORGANISMS OBTAINED THEREWITH, PEPTIDE AMIDASES CONTAINED IN THEM AND USE THEREOF

(75) Inventors: Ursula Stelkes-Ritter, Niederzier; Maria-Regina Kula, Hambach-Niederzier; Klaudia Wyzgol, Dusseldorf; Andreas Bommarius, Frankfurt; Michael Schwarm, Alzenau; Karlheinz Drauz, Freigericht, all of (DE)

(73) Assignee: Degussa Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/382,590

(22) Filed: Aug. 25, 1999

Related U.S. Application Data (62) Division of application No. 08/737,483, filed on Feb. 21, 1997, now Pat. No. 5,985,632.

(30) Foreign Application Priority Data

May 9, 1994 (DE) ................................................ 44 159 714
Apr. 29, 1995 (WO) ................................... PCT/EP95/01689

(51) Int. Cl.$^7$ ................................ C12N 9/02; C12N 9/48
(52) U.S. Cl. .......................... 435/71.2; 435/189; 435/212
(58) Field of Search .................................. 435/71.2, 189, 435/212

(56) References Cited

U.S. PATENT DOCUMENTS 5,215,897 * 6/1993 Sakashita .............................. 435/106
5,238,838 * 8/1993 Kula ..................................... 435/228
5,369,016 11/1994 Steinke et al. .

FOREIGN PATENT DOCUMENTS 36 29 242 3/1987 (DE) .
40 14 564 7/1991 (DE) .

OTHER PUBLICATIONS

Nawaz et al., Can. J. Microbiol., 1993, 39(2), 207–12.*
Nawaz et al., Can. J. Microbiol., 1993, 39(2), pp. 207–212.
Stelkes–Ritter et al., "Characterization of a newly screened microbial peptide amidase", Proceedings of the 5$^{th}$ Akabori Conference, 1994.
K. Breddam et al., Carlsberg Res. Commun., 49 (1984), pp. 535–554.
Nishida et al., Enzyme Microb. Technol., 6 (1984), pp. 85–90.

* cited by examiner

Primary Examiner—Irene Marx
(74) Attorney, Agent, or Firm—Pillsbury Winthrop LLP (57) ABSTRACT

A plant peptide amidase from the flavedo of oranges is known; this can be obtained only in small quantities and is seasonal. The proposed new enzymes are microbial peptide amidases which can be obtained from micro-organisms recovered from soil samples in a "double screening" and grown. These microbial peptide amidases are particularly useful for (a) the production of peptides and N-terminal-protected amino acids, (b) racemate splitting of N-protected amino acid amides, (c) obtaining non-proteinogenous D-amino acids, and (d) obtaining new N$_\alpha$-protected D-amino acid amides.

5 Claims, 5 Drawing Sheets

PROCESS FOR OBTAINING MICROORGANISMS CONTAINING PEPTIDE AMIDASE, MICROORGANISMS OBTAINED THEREWITH, PEPTIDE AMIDASES CONTAINED IN THEM AND USE THEREOF

This is a division of application Ser. No. 08/737,483, filed Feb. 21, 1997 now U.S. Pat. No. 5,985,632.

This application is based on application Ser. No. 44159714, filed in Germany on May 9, 1994, and PCT/EP95/01689, filed Apr. 29, 1995, the contents of each of which are hereby incorporated by reference.

BACKGROUND OF THE INVENTION

1. Field of the Invention

The invention relates to a process for obtaining microorganisms containing peptide amidase, microorganisms obtained therewith, peptide amidases contained in them and the use thereof.

The invention relates in particular to a screening process for microorganisms exhibiting peptide amidase activity in accordance with the generic part of claim 1; microorganisms obtained according to this process and deposited in conformity with claims 2–4; peptide amidases which can be isolated from the microorganisms according to claims 5–7 and the use thereof.

2. Background information

The following publications are cited regarding the state of the art:

(1) DE-OS 36 29 242, (2) K. Breddam, Carlsberg Res. Commun. 49 (1984) 535–554, (3) DE patent 40 14 564 and (4) Y. Nishida et al., Enzyme Microb. Technol., 6 (1984), 85–90.

A peptide amidase is an enzyme which catalyzes the selective hydrolysis of a C-terminal amide function in a peptide amidase, that is, accelerates the following conversion:

(I)

Here, R' signifies a protective group for n=0 and for n>0 any amino acid, a protective group or H; n stands for zero or any whole number, $R_x$ are the side chains of the amino acids for n>0 whereas $R_1$ signifies the side chain of the C-terminal amino acid.

The selective splitting off of the C-terminal amino group of peptide amides is generally difficult to achieve by a chemical conversion since the peptide bond is also subject to a hydrolytic attack. This results in mixtures which are difficult to separate and in low yields.

Reference (1) teaches amidases for an enzymatic splitting off of the acid amide group which, on account of their a-amino acid amidase activity, can only be used, however, for the production of L-amino acids from a-unprotected D,L-amino acid amides. Peptide amides are not accepted.

Reference (4) teaches the continuous production of N-Ac-L-Met from N-Ac-D,L-methionine amide in an enzymatic process using Erwinia carotovera.

Erwinia carotovera does contain an amidase activity; however, it is limited exclusively to amides of methionine. Thus, the enzyme from Erwinia carotovera only "splits off amino acid amide" and is not a peptide amidase. Furthermore, the enzyme from Erwinia carotovera can obviously only convert N-acetylated amino acid amides, in which conversion it is a disadvantage that the Ac protective group can only be split off with difficulty or not at all.

On the other hand, peptidases are known which catalyze the hydrolytic splitting of the peptide bonds and of which it is only known that they have a certain secondary activity for splitting off the C-terminal amide protective group. An example of this is the carboxy peptidase Y, especially in chemically modified form (see reference (2)).

Thus, all these processes have serious disadvantages.

The state of the art according to reference(3) is also a peptide amidase which can be isolated from the flavedo of citrus fruits, especially of oranges. The peptide amidase described does not attack the peptide bond and catalyzes the splitting off of the free amino group from peptide amides. The peptide amidase known from (3) is characterized by the following parameters:

Splitting off of the C-terminal amino group from peptide amides and N-terminally protected amino acid amides;

No splitting of peptide bonds;

Optimum pH at 7.5±1.5;

Good stability in the pH range between pH 6.0 and pH 9.0;

The optimum temperature is 30° C. at a pH of 7.5;

Slight inhibition by inhibitors from serine proteases, especially phenylmethane sulfonyl fluoride;

The molecular weight is 23,000±3,000;

Aggregate formation is occasionally observed;

The isoelectric point is approximately pH 9.5;

The enzyme does not accept any D-amino acid groups in C-terminal position and the rate of hydrolysis thereby is distinctly less than in the case of L-amino acid groups.

However, the isolated enzyme can be obtained from flavedo only in slight amounts and as a function of the season. More extensive studies also did not succeed, in spite of an approximately 500-fold enrichment, in preparing the protein in homogeneous form, so that molecular and genetic studies for improving the enzyme production were not able to be included due to lack of data.

However, this also renders the suggestion given in reference (3) moot—that a microbial production of the enzyme can be achieved in a known manner by gene technology manipulation. The problems in the presentation of the homogeneous form do not allow manipulations of gene technology.

SUMMARY OF THE INVENTION

Therefore, in view of the problems associated with the state of the art, the invention has the object of making available a process for isolating microorganisms containing peptide amidase which makes possible a rapid selection of suitable strains. A further object is also a stable peptide amidase which is more readily available than the known peptide amidase from flavedo at an equally high selectivity of the hydrolytic splitting off of the free amino group on the C-terminal end of peptide amides.

These objects and others not cited in detail are achieved by a process with the features recited in claim 1.

Microorganisms can be produced at practically any time of the year in any desired amount. Therefore, collection strains and isolated strains which can mobilize amide nitrogen as a source of nitrogen are analyzed for peptide amidase activity in a limited screening. Z-Gly-Tyr-$NH_2$ was used as test substrate and the expected hydrolysis product Z-Gly-Tyr-OH determined by HPLC.

It is possible, by first incubating specimens containing microorganisms in a "double screening" in a nutrient medium containing amide nitrogen as nitrogen source and inoculating colonies subsequently produced onto a nutrient medium containing N-acetyl-D,L-methionine amide, then incubating them and selecting the microorganisms which grow in both nutrient media, to find strains with an unusually good rate of success which are both relatively stable and also selective and active.

For the screening for microorganisms which can utilize amide nitrogen, samples of soil were suspended 4–6 hours in isotonic solution of common salt. The samples of soil were of any origin, including garden soil, forest soil, loamy or sandy soil. The solids were separated off at 2000 rpm by centrifugation. The supernatant was spread out onto agar plates and used to inoculate liquid media in Erlenmeyer flasks. The plates were incubated 3–7 days at 30° C. and the Erlenmeyer flasks agitated at the same temperature at 120 rpm. Then, individual cultures were isolated from the plates and brought into pure culture by being multiply spread out. After this time aliquots were taken from the incubated Erlenmeyer flasks and fresh medium inoculated therewith. This process was repeated up to five times before specimens of the culture liquid were spread out after a suitable dilution onto plates. The nutrient medium for the solid and also for the liquid medium had the following composition:

| | |
|---|---|
| $K_2HPO_4$ | 2.50 g/l |
| $KH_2PO_4$ | 1.95 g/l |
| NaCl | 1.00 g/l |
| $CaCl_2*2H_2O$ | 0.05 g/l |
| $MgSo_4*7H_2O$ | 0.3 g/l |
| Yeast extract | 0.50 g/l |
| DL-carnitine amide | 5.00 g/l |
| Trace saline solution | 0.80 ml/l |
| Vitamin solution | 2.5 ml/l |
| (Agar for solid media | 18.0 g/l) |
| pH 7.2 | |

$CaCl_2*2H_2O$, $MgSO_4*7H_2O$ as well as DL-carnitine amide and the vitamin solution (see below) were sterilized by filtration and added to the autoclaved, cooled-down medium. The trace saline solution was composed as follows:

| | |
|---|---|
| $H_3BO_3$ | 75.0 mg |
| $MnCl_2*4H_2O$ | 50.0 mg |
| $ZnCl_2$ | 187.0 mg |
| $CuSO_4*5H_2O$ | 50.0 mg |
| $FeCl_3*6H_2O$ | 625.0 mg |
| $(NH_4)_8Mo_7O_{24}*4H_2O$ | 25.0 mg |
| $CoSO_4*7H_2O$ | 37.5 mg |
| $H_2O$ demin. | ad. 0.2 l. |

Individualized microorganisms grown on this medium were used for screening for organisms with peptide amidase activity.

For screening for microorganisms with peptide amidase activity, a part of the organisms obtained above were spread out onto agar nutrient media and incubated 2 days at 30° C. In order to obtain higher cell masses, the cultures were enriched in 100 ml Erlenmeyer flasks with 20 ml medium. The incubation took place at 30° C. for 2 days at 120 rpm. The nutrient medium used for this had the following composition:

| | |
|---|---|
| $K_2HPO_4$ | 0.50 g/l |
| $KH_2PO_4$ | 2.00 g/l |
| NaCl | 1.00 g/l |
| $CaCl_2*2H_2O$ | 0.05 g/l |
| $MgSo_4*7H_2O$ | 0.10 g/l |
| Glucose | 5.00 g/l |
| DL-carnitine amide | 1.00 g/l |
| N-Ac-DL-Met-$NH_2$ | 2.00 g/l |
| Yeast extract | 0.50 g/l |
| Vitamin solution | 2.50 ml/l |
| Trace saline solution | 0.80 ml/l |
| (Agar for solid media | 18.00 g/l) |
| pH 7.3. | |

N-Ac-D,L-Met-$NH_2$ was used as inductor thereby. Glucose should be avoided as a source of carbon so that the inductor is attacked from the N-terminus. Amides, glucose, $CaCl_2*2H_2O$, $MgSo_4*7H_2O$ and the vitamin solution were sterilized by filtration and added to the autoclaved, cooled-down nutrient medium (see below for the composition of the trace saline solution and of the vitamin solution).

The cells were centrifuged, washed with 50 mM tris/HCl, pH 7.5 and taken up in this buffer (20–40% cell suspension). The cell maceration took place by wet grinding with glass beads 0.3 mm in diameter.

The raw extracts obtained therefrom were analyzed for the capacity to hydrolyze Z-Gly-Tyr-$NH_2$.

Of 45 strains analyzed for deamidation, 6 exhibited the capacity to convert Z-Gly-Tyr-$NH_2$ to Z-Gly-Tyr-OH. Table 1 shows selected data from the screening for peptide amidases.

TABLE 1

| Strain No. | $OD_{660}$ * | Protein content (mg BSAeq/ml) | Spec. Activity (mU/mg BSAeq) |
|---|---|---|---|
| 4 | 0.98 | 1.93 | 4.84 |
| 11 | 1.22 | 5.30 | 9.70 |
| 18 | 1.13 | 5.96 | 2.97 |
| 21 | 0.87 | 7.90 | 5.22 |
| 22 | 1.04 | 9.40 | 7.23 |
| 42 | 1.58 | 3.46 | 2.82 |

* $OD_{660}$ = Optical density at a wavelength of 660 nm.

Isolated strains 4, 11, 18, 21, 22, 42 were deposited pursuant to the Budapest Treaty in the German Collection for Microorganisms (address Mascheroder Weqlb, D-38124 Braunschevera, Germany) DSM under the name of the applicant.

| Strain No. | DSM Deposit No. | Deposition date |
|---|---|---|
| 4 | 9182 | 5-2-1994 |
| 11 | 9181 | 5-2-1994 |
| 18 | 9183 | 5-2-1994 |

-continued

| Strain No. | DSM Deposit No. | Deposition date |
|---|---|---|
| 21 | 9184 | 5-2-1994 |
| 22 | 9185 | 5-2-1994 |
| 42 | 9186 | 5-2-1994 |

Strain 11 was selected from the deposited strains for further analyses. Strain 11 was determined by the DSM as Stenotrophomonas maltophilia (*Xanthomonas maltophilia*). Strains 4, 18, 21, 22 and 42 were also evaluated, with the result that strains 4, 18, 21 and 22 were likewise identified as Stenotrophomonas maltophilia (*Xanthomonas maltophilia*) and strain 42 as Ochrobactrum anthropi.

The invention also has as subject matter peptide amidases obtainable from the screened microorganisms.

The peptide amidase is formed intracellularly and can be isolated from the cells and purified according to processes familiar to the expert in the art.

The microbial peptide amidase is characterized by the following parameters:

Splitting off of the C-terminal amino group from peptide amides and N-terminally protected amino acid amides;
No splitting of peptide bonds;
Optimum pH at 6.0±0.5;
Good stability in the PH range between pH 7 and pH 8;
The optimum temperature is 35–40° C. at a pH of 7.5;
Inhibition of serine groups by inhibitors such as phenyl-methane sulfonylfluoride as well as in particular 4-(2-aminoethylbenzylsulfonylfluoride) (Pefabloc);
The molecular weight is approximately 38,000 daltons (determined by gel filtration);
The isoelectric point is approximately pH 5.8.

The invention also comprises the isozymic forms of the microbial peptide amidase in accordance with the invention. The term "isozymic forms" in this connection denotes the enzymes in other microorganisms which catalyze the same reaction as the peptide amidase from *Xanthomonas maltophilia*.

Table 2 indicates some data for the purification of the peptide amidase from *Xanthomonas maltophilia*.

TABLE 2

|  | Spec. activity (mU/mg BSAeq) | Purification (-) | Yield (%) |
|---|---|---|---|
| Raw extract | 4 | 1 | 100 |
| Q-sepharose FF + ultrafiltration | 224 | 56 | 97 |
| Superdex G 75 + ultrafiltration | 1034 | 256 | 75 |
| IEF on the Mono P | 2133 | 533 | 63 |

The purified peptide amidase from *Xanthomonas maltophilia* has in particular the following characteristic properties:

Purification of >500 at a yield of >60%
A molecular weight of 38000 da (gel filtration)
The isoelectric point is approximately pH 5.8
Temperature optimum between 37–45° C.
pH optimum between 5–6.5
Temperature-stable at 20, 30 and 37° C. over 3 days
At pH 7–8 the enzyme is stable at 30° C. over 7 days
Upon the addition of 20% DMF the peptide amidase exhibits after 24 h a residual activity of 32% at a pH of 7.5
Serine group decisive for enzyme activity.

The N-terminal initial sequence of the peptide amidase from *Xanthomonas maltophilia* (set forth in SEQ ID NO: 1) is:

| AS 1 | X |
|---|---|
| AS 2 | Arg |
| AS 3 | Asn |
| AS 4 | Val |
| AS 5 | Pro |
| AS 6 | Phe |
| AS 7 | Pro |
| AS 8 | Tyr |
| AS 9 | Ala |
| AS 10 | Glu |
| AS 11 | Thr |
| AS 12 | Asp |
| AS 13 | Val |
| AS 14 | Ala |
| AS 15 | Asp |
| AS 16 | Leu |
| AS 17 | Gln |

The first amino acid could not be determined. No comparable sequence could be determined in the program Genepro 5.0 of the databank PIR, version 30.

The following table 3 compares the properties of the known, vegetable peptide amidase from flavedo of oranges (PAF) and of the microbial peptide amidase of the invention from Xanthomonas (PAX).

The peptide amidase of the invention shows in it neither peptidase activity nor amino acid amidase activity.

TABLE 3

|  | PAF | PAX |
|---|---|---|
| Spec. activity (U/mg BSAeq) | 100.1 | 2.13 |
| Amino acid amidase activity | 0 | 0 |
| Peptidase activity | 0 | 0 |
| Molar mass (gel filtration) | 23000 | 38000 |
| pH optimum | 6.5–8.7 | 5–6.5 |
| Temperature optimum | 30–35° C. | 37–45° C. |
| Isoelectric point | 9.5 | 5.8 |
| N-terminal sequence | not known |  |

The microbial peptide amidases belonging to the invention are very advantageously suited for the catalysis of quite a number of reactions.

Thus, the microbial peptide amidases of the invention can be used with success to produce peptides and N-terminally protected amino acids of the general formula II (II)

in which R' is a protective group or any peptidically or isopeptidically bound amino acid- or peptide group and $R_1$ signifies hydrogen or any side chain with enzymatic splitting off of a C-terminal amino group from a peptide amide or from an N-terminally protected amino acid amide.

In a preferred variant of the process, this enzymatic reaction is carried out in a continuous manner.

It is also preferred that the deamidation is carried out as a process step of a coupled conversion with an enzyme system comprising proteases, peptidases, esterases and/or lipases. In this connection the selectivity of the peptide amidases of the invention is especially advantageous.

The microbial peptide amidases can also be used in accordance with the invention in processes for producing peptides of the above-mentioned type by the enzymatic conversion of optionally N-protected amino acid alkyl esters or optionally N-protected peptide alkyl esters with amino acid amides in aqueous phase or an aqueous-organic environment. The reaction takes place thereby in the presence of an enzyme which brings about the peptidic bonding and under enzymatic splitting off of the amide protective group; the synthesis is allowed to take place in a continuous manner, the peptide amide hydrolyzed by the peptide amidase enzymatically to the peptide and finally the peptide is separated on account of its charge from the reaction mixture and the amino acid amide returned.

Furthermore, the microbial peptide amidase of the invention can also be used for the splitting [separation] of racemic mixtures of N-protected amino acid amides in which a racemic mixture of N-protected amino acid amides is incubated with the peptide amidase and is reacted until the complete conversion of the N-protected L-amino acid amide, and subsequently the N-protected L-amino acid is separated from the N-protected D-amino acid amide based on the differences of charge. Furthermore, according to the invention D-amino acids can also be produced. Thus, the $N_\alpha$-protected L-amino acid amide can be selectively and enzymatically hydrolyzed, for example, within the scope of the invention by using the microbial peptide amidase of the invention, the $N_\alpha$-protected D-amino acid amide separated and converted by acid hydrolysis into the free D-amino acid. The amino acid amide racemates useful for the invention include, among others, $N_\alpha$-formyl-DL-methionine amide, $N_\alpha$-methylaminocarbonyl-DL-methionine amide, $N_\alpha$-methoxycarbonyl-DL-methionine amide, $N_\alpha$-ethoxycarbonly-DL-methionine amide, $N_\alpha$-benzyloxycarbonyl-DL-methionine amide, $N_\alpha$-acetyl-DL-neopentylglycine amide, $N_\alpha$-benzyloxycarbonyl-DL-neopentylglycine amide.

Finally, the microbial peptide amidases of the invention can also be used with great advantage to obtain non-proteinogenous D-amino acids, preferably using sterically demanding, N-protected racemic amino acid amides such as N-acetyl-neopentylglycine amide, N-acetyl-naphthylalanine amide, N-acetylphenylglycine amide or similar derivatives. The N-acetyl-L-amino acid amides are enzymatically hydrolyzed, the N-acetyl-D-amino acid amides separated from the reaction mixture by chromatography and finally converted by acid hydrolysis into the free D-amino acids.

The $N_\alpha$-protected D-amino acid amides obtainable by using the microbial peptide amidase of the invention from the preferred racemic, $N_\alpha$-protected amino acid amides include, for example: $N_\alpha$-formyl-D-methionine amide, $N_\alpha$-methylaminocarbonyl-D-methionine amide, $N_\alpha$-methoxycarbonyl-D-methionine amide, $N_\alpha$-ethoxycarbonyl-D-methionine amide, $N_\alpha$-benzyloxycarbonyl-D-methionine amide, $N_\alpha$-acetyl-D-neopentyiglycine amide, and $N_\alpha$-benzyloxycarbonyl-D-neopentylglycine amide.

DETAILED DESCRIPTION OF THE INVENTION

The invention is explained in the following in detail using examples. Further embodiments and particularities also result in particular from the attached figures, to which reference is made in the specification.

EXAMPLE 1

Production and Workup of the Peptide Amidase from *Xanthomonas Maltophilia*

1.1 Growth 40 g moist biomass/l and an activity of 4 U/l were obtained in the partially optimized medium with the following composition. The media optimization took place with the aid of the genetic algorithm. The nutrient medium was autoclaved, glucose, N-Ac-DL-Met-$NH_2$, $CaCl_2*2H_2O$, $MgSO_4*7H_2O$ and the vitamin solution were added in a sterile manner.

| | |
|---|---|
| N-Ac-D, L-Met-$NH_2$ | 4.3 g/l |
| Yeast extract | 4.5 g/l |
| Peptone from casein | 19.7 g/l |
| Glucose | 18.4 g/l |
| $KH_2PO_4$ | 0.5 g/l |
| $K_2HPO_4$ | 2.0 g/l |
| NaCl | 1.0 g/l |
| $CaCl_2*2\ H_2O$ | 0.05 g/l |
| $MgSo_4*7\ H_2O$ | 0.1 g/l |
| Vitamin solution according to Schlegel* | 2.5 ml/l |
| Trace saline solution | 0.8 ml/l |
| (Agar in the case of solid media | 18.0 g/l) |
| Trace saline solution | |
| $H_3BO_3$ | 75.0 mg |
| $MnCl_2*4H_2O$ | 50.0 mg |
| $ZnCl_2$ | 187.0 mg |
| $CuSO_4*5H_2O$ | 50.0 mg |
| $FeCl_3*6H_2O$ | 625.0 mg |
| $(NH_4)_6Mo_7O_{24}*4H_2O$ | 25.0 mg |
| $CoCl_2*6H_2O$ | 37.50 mg |
| $NiCl_2*6H_2O$ | 50.00 mg |
| $H_2O$ | ad 0.2 l |

*Schlegel, H.G. (1985): Allgemeine Mikrobiologie [German - General Microbiology], Thieme Verlag, Stuttgart 1.2 Cellular maceration The cell maceration took place by the wet grinding of a 20–40% cellular suspension in 50 mM tris/HCl buffer, pH 7.5 with glass beads Ø 0.3 mm. The glass beads and the cellular fragments were separated by centrifugation. The glass beads were then re-suspended in 50 mM tris/HCl, pH 7.5 and separated again by centrifugation. The supernatants were purified and constituted the raw extract for the workup described in the following. The cellular maceration was evaluated by determining the amount of protein released according to Bradford (Bradford, M. M. (1976), Anal. Biochem., 72, 248–254) and by microscopic observation.

1.3 Purification 1.3.1. Ion exchange Chromatography

As the first step in the purification of the peptide amidase from *Xanthomonas maltophilia*, an anion exchange chromatography was carried out on Q-sepharose Fast Flow (Pharmacia, Uppsala). The following conditions applied for the anion exchanger:

| Column | 10 cm * π * 1.3 * 1.3 * cm$^2$ = 53 ml Q sepharose FF (Pharmacia, Uppsala) |
|---|---|
| Travel rate | 10 ml/min |
| Equilibration | 50 mM tris, 20 mM KCl, pH 8.0 |
| Specimen charging | 77.2 ml raw extract à 6.8 mg BSAeq/ml |
| Washing | 50 mM tris/HCl, 20 mM KCl, pH 8.0 |
| Elution | Linear gradient with rising salt content 200 ml 50 mM tris, 20 mM KCl, pH 8.0 20 ml 50 mM tris, 200 mM KCl, pH 8.0 |

The detection took place at 280 nm, the fractions were trapped at 10 ml each. The peptide amidase was able to be eluted at a salt content of 80–120 mM KCl from the anion exchanger. The active fractions were pooled and concentrated with the aid of an Amicon ultrafiltration cell with a YM 10 membrane to 2 ml for the following gel filtration.

1.3.2 Gel filtration

The active fractions of the anion exchange chromatography were concentrated as described and subjected to a gel filtration on Superdex G 75 material (Pharmacia, Uppsala). The following conditions applied for the gel filtration:

| Column | 60 cm * π * 0.8 * 0.8 * cm$^2$ = 120.6 ml |
|---|---|
| Travel rate | 1 ml/min |
| Equilibration | 50 mM tris, 150 mM KCl, pH 7.5 |
| Specimen | 2 ml à 4.55 mg BSAeq/ml of the concentrated active fractions of the anion exchange chromatography |
| Elution | 50 mM tris, 150 mM KCl, pH 7.5 |
| Fraction size | 1 ml |
| Detection | 280 nm |

The active fractions of the gel filtration were pooled and concentrated via a YM 10 membrane in an Amicon ultrafiltration cell to 1 ml (1.47 mg BSAeq/ml) and were available in this manner for the following isoelectric focusing.

1.3.3 Isoelectric Focusing

The active fractions of the gel filtration and those of the gel filtration evaporated to 1 ml as described under 1.3.2 were purified with the aid of isoelectric focusing. The conditions for this are presented in the following.

| Column | 5.1 cm * 0.25 * 0.25 * cm$^2$ * π = 1 ml Mono P (Pharmacia, Uppsala) |
|---|---|
| Travel rate | 1 ml/min |
| Equilibration | 25 mM triethanol amine, pH 8.0 |
| Specimen | 1 ml of the concentrated active fractions of the gel filtration (re-buffered with 25 mM triethanol amine, pH 8.0, 1.47 mg BSAeq/ml) |
| Washing | 25 mM triethanol amine, pH 8.0 |
| Elution | 10 mM linear pH gradient from A to B Eluent A: 25 mM triethanol amine, pH 8.0 Eluent B: Polybuffer 74 (diluted 1:10, Pharmacia), pH 5.0 |
| Fractions | 0.5 ml |
| Detection | 280 nm |

In the first two steps of the purification (anion exchange chromatography and gel filtration) interfering protease/peptidase activities were completely removed. After the isoelectric focusing, a preparation enriched 533-fold was obtained. A main band which is enzymatically active is observed in the native gel. The N-terminal sequence was determined by means of a liquid-phase sequenator (Applied Biosystems 470 with on-line HPLC coupling) after elution of the band out of the native gel.

EXAMPLE 2

Characterization of the Enzyme pH Optimum and pH Stability

Figure 1:
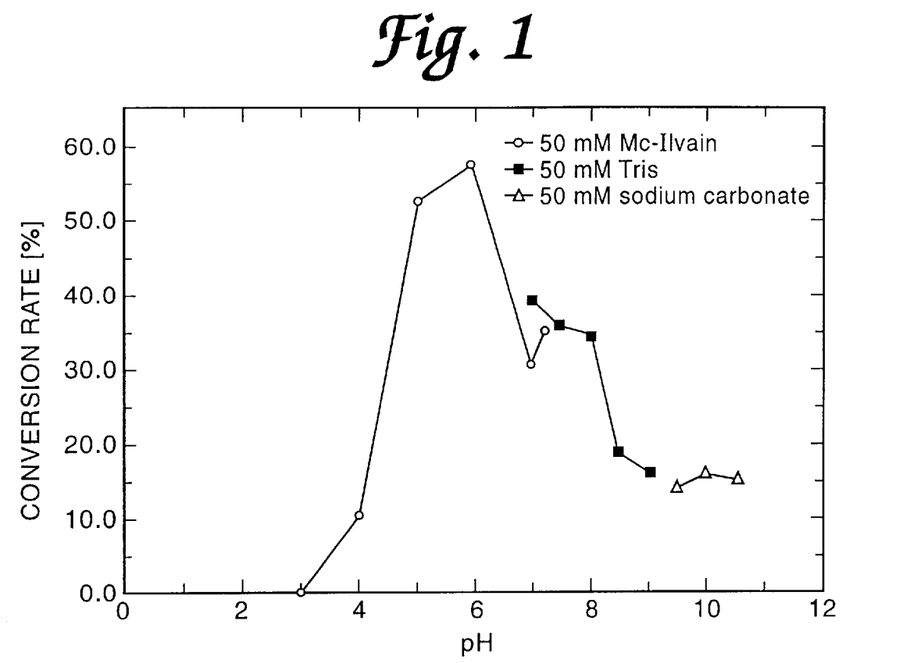
FIG. 1 shows the dependency of the conversion rate (%) on the pH for peptide amidase obtained from *Xanthomonas maltophilia*.

FIG. 1 shows the dependency of the conversion rate in % on the pH. 50 mM Mc-Ilvain buffer were used in the pH range of 3.0–7.25, 50 mM tris/HCl buffer between pH 7.0–9.0 and for the basic pH range of 9.5–10.5 50 mM Na$_2$CO$_3$ buffer. The test batch of 1 ml was composed as follows:

| 100 µl | 100 mM Z-Gly-Tyr-NH$_2$ (dissolved in H$_2$O/dimethylformamide in a 1:1 ratio) |
|---|---|
| 200 µl | Enzyme solution à 63 µg BSAeq/ml of the purification stage after the gel filtration |
| 700 µl | Buffer. |

A pre-incubation took place without the addition of substrate for 5 min at 30° C. The reaction was then started by adding 100 µl substrate and incubated 4 hours at 30° C. In order to stop the reaction, 100 µl of the reaction batch were removed and compounded with 100 µl glacial acetic acid as well as 1.4 ml HPLC mobile solvent (see 1.4 standard assay of peptide amidase).

FIG. 1 shows the results of the analysis of the pH optimum. The pH optimum of the peptide amidase peptide amidase from *Xanthomonas maltophilia* results at 6.0±0.5.

Figure 2:
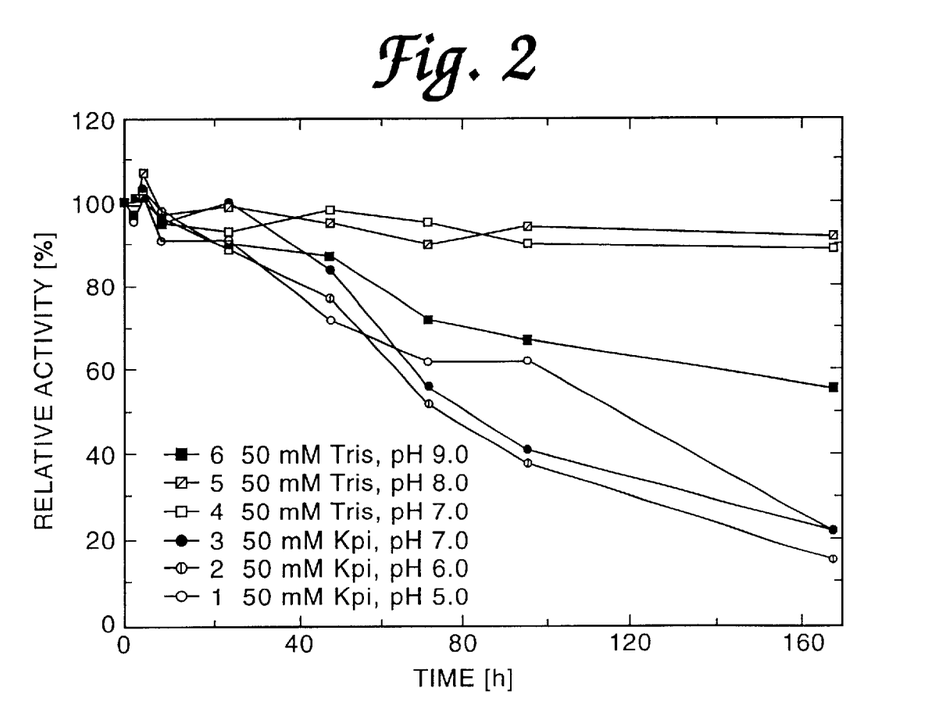
FIG. 2 shows a plot of relative activity vs. time for peptide amidase from *Xanthomonas maltophilia* in various buffers at 30° C.

The relative activity (%) as a function of the time (h) was determined for the pH stability of peptide amidase from *Xanthomonas maltophilia*. 50 mM Kp$_i$ buffer was used for the pH range of 5.0–7.0 and 50 mM tris/HCl buffer between 7.0–9.0. For the analyses of pH stability 100 µl enzyme solution à 0.73 mg BSAeq/ml (purification stage after the gel filtration) were incubated with 900 µl buffer of differing pH at 30° C. Specimens were drawn at different times and the activity determined with Z-Gly-Tyr-NH$_2$ as substrate. The results are shown in FIG. 2. A good stability results in the range of pH 7–pH 8.

EXAMPLE 3

Temperature Optimum and Temperature Stability

Figure 3:
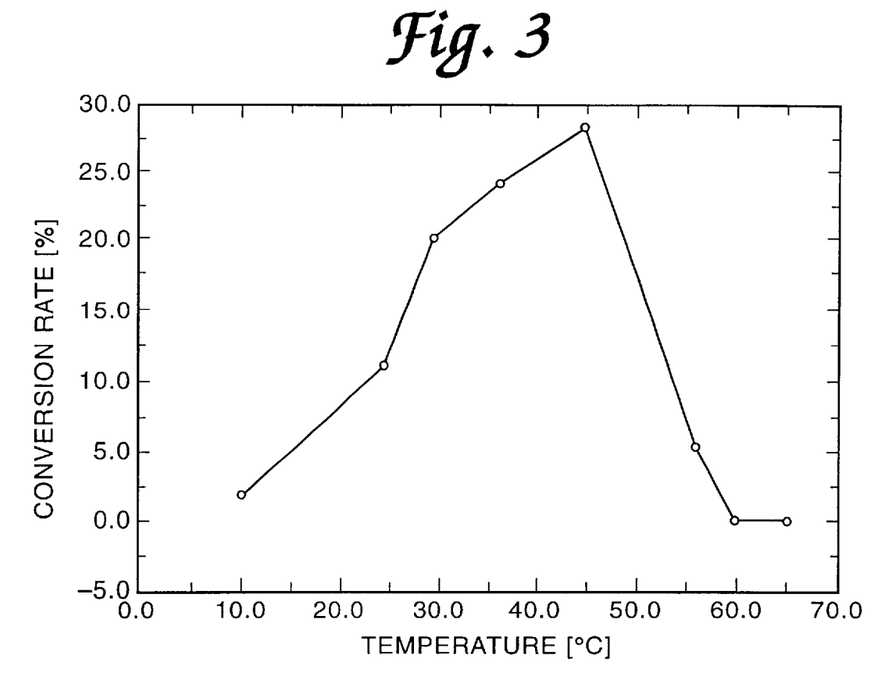
FIG. 3 shows a plot of the conversion rate as a function of the temperature for peptide amidase from *Xanthomonas maltophilia*.

The temperature optimum of peptide amidase from *Xanthomonas maltophilia* was determined. To this end 200 µl enzyme solution à 63 μg BSAeq/ml of the purification stage after the gel filtration were compounded with 700 μl of the 50 mM tris/HCl buffer pre-tempered to the particular temperature and the reaction started with 100 μl Z-Gly-Tyr-NH$_2$ (10 mM in the test batch). Aliquots of 100 [mycro]l were stopped after 2 h with 100 μl glacial acetic acid and the activity determined corresponding to 1.4. The result is shown in FIG. 3. The temperature optimum was approximately 35–40° C. at a pH of 7.5.

Figure 4:
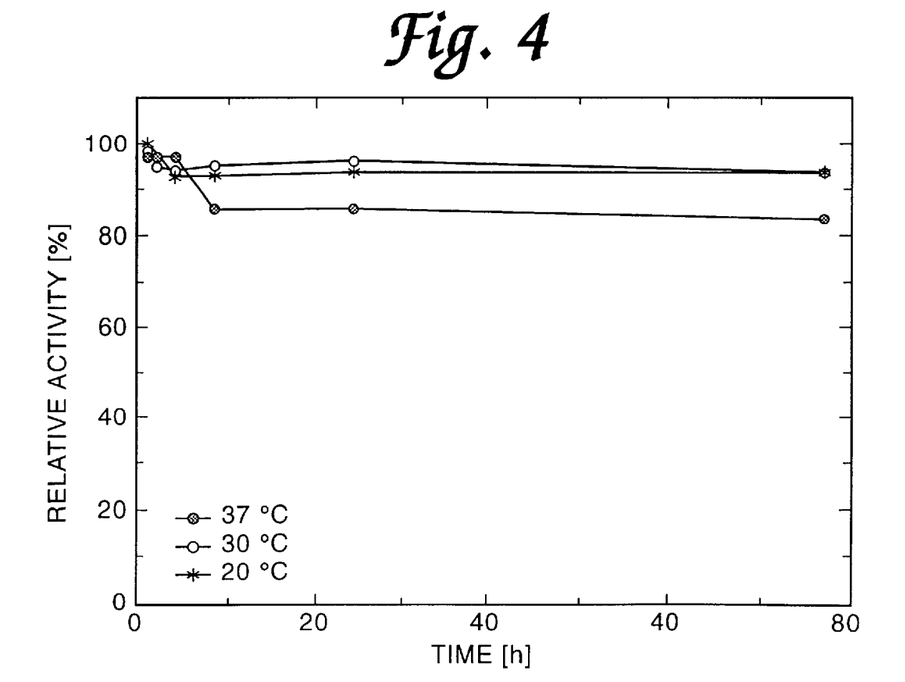
FIG. 4 shows the temperature stability of the peptide amidase from *Xanthomonas maltophilia*.

The relative activity (%) as a function of the time (h) was determined for the temperature stability of peptide amidase from *Xanthomonas maltophilia*. To this end 100 μl enzyme solution & 0.73 mgBSAeq/ml were compounded with 900 μl pre-tempered 50 mM tris/HCl buffer and incubated at 20, 30, 37 and 56° C. Specimens were drawn at different times and the activity determined with Z-Gly-Tyr-NH$_2$ as substrate. The results are shown in FIG. 4. Whereas the enzyme is inactivated at 56° C. after only a few minutes, it proves to be extremely stable at 20, 30 and 37° C.

EXAMPLE 4

Enzyme Kinetics of Peptide Amidase

The dependency of the reaction rate of peptide amidase from *Xanthomonas maltophilia* on the substrate concentration (Z-Gly-Tyr-NH$_2$) was determined and the kinetic parameters determined from the data according to Marquardt. To this end, 50 μl enzyme solution à 27 μg BSAeq/ml were compounded with 400 μl 50 mM tris/HCl buffer, pH 7.5. The reaction was started by adding Z-Gly-Tyr-NH$_2$ as substrate. The substrate was present in the reaction batches in a concentration range of 0.4 to 20 mM. The incubation took place for 2 hours at 30° C. The enzyme activity was then determined as described under 1.4. The $K_m$ value was determined with 0.82 mM and $v_{max}$ with 0.53 U/mg BSAeq.

Figure 5:
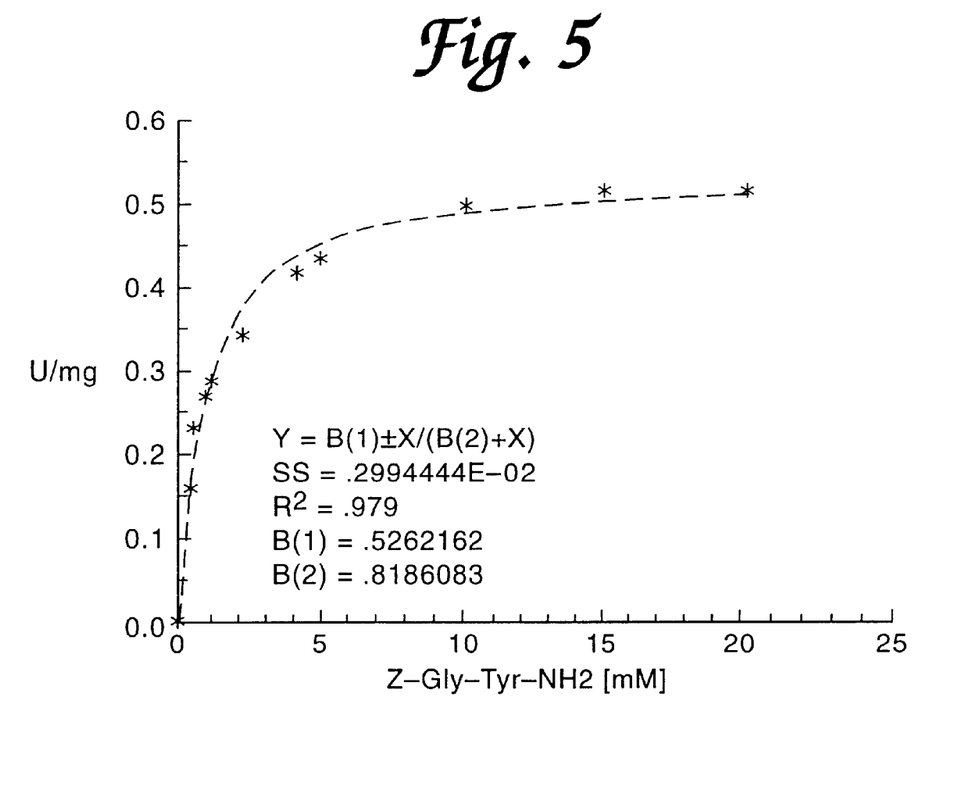
FIG. 5 shows the kinetic determination of the conversion of Z-Gly-Tyr-$NH_2$ with the peptide amidase from *Xanthomonas maltophilia*.

FIG. 5 shows the reaction rate of the deamidation of Z-Gly-Tyr-NH$_2$ as a function of the substrate concentration.

1.4 Standard Assay of Peptide Amidase

The reaction conditions were selected with a view to the pH stability of peptide amidase from *Xanthomonas maltophilia*.

Standard Assay of Peptide Amidase

| | |
|---|---|
| 50 mM tris/HCl, pH 7.5 | 350–700 μl |
| Enzyme solution | 100–200 μl |
| 100 mM Z-Gly-Tyr-NH$_2$ dissolved in buffer/DMF 1:1 (10 mM in the test) | 50–100 μl |
| Test batch | 500–1000 μl |
| Temperature | 30° C. |
| Incubation time | variable |

In order to stop the reaction 100 μl of the reaction solution was removed, compounded with 100 μl glacial acetic acid and filled with 1.4 ml HPLC mobile solvent. An aliquot of 20 μl was analyzed by HPLC. The conditions for the HPLC analysis of Z-Gly-Tyr-NH$_2$ were as follows:

| | |
|---|---|
| Mobile solvent: | 65% 10 mM TBA-sulfate (tetrabutyl ammonium sulfate) 35% acetonitrile |
| Travel rate | 1 ml/min |
| Travel time | 10 min |
| Detection | 280 nm |
| Elution | isocratic |
| Column | RP-18, ODS Hypersil (5 μm) |
| Retention times | Z-Gly-Tyr-NH$_2$  4.5 min |
| | Z-Gly-Tyr-OH  5.9 min |

Example 5

Substrate spectrum 18 mU of peptide amidase (purification state after the gel filtration) per ml test batch was used for the substrate spectrum of peptide amidase from *Xanthomonas maltophilia*. The concentration of the tested substrates was 10 mM in the reaction batch. Unless otherwise indicated, L-amino acid derivatives were used. The incubation took place in 50 mM tris/HCl, pH 7.5 at 30° C. for 3 hours. The reaction was stopped by heating for 5 minutes at 95° C. The determination of activity took place using enzymatic determination of the released ammonia (Bergmeyer, U. (1985): Methods of Enzymatic Analysis, p. 459, VCH Verlagsgesellschaft, Weinheim). Table 4a shows the conversion of dipeptide amides, table 4b the conversion of N-acetylamino acid amides and table 4c the influence of the N-terminal protective groups and of the amino acid adjacent to the C terminus.

The following thin-layer chromatographic methods were used for the analysis of the substrates and products cited in table 4d. To this end 1 μl of the stopped reaction batch was applied.

| | |
|---|---|
| Stationary phase | DC aluminum foil 60 F$_{254}$ (20 * 10 cm$^2$) |
| Mobile phase | Pyridine/butanol/glacial acetic acid/water (12:15:3:5) |
| Detection | Ninhydrin (0.3% in propan-1-ol) The color development took place for approximately 3 min at 100° C.) |

The following HPLC separating conditions applied for the analysis of the conversion of longer-chain peptides shown in table 4e:

| | | Retention time | | |
|---|---|---|---|---|
| Substrate | Mobile solvent* | amide (min) | acid | Wavelength (nm) |
| Z-Pro-Leu-Gly-NH$_2$ | 60/40 | 6.0 | 7.3 | 256 |
| Z-Gly-Gly-Leu-NH$_2$ | 60/40 | 4.9 | 6.0 | 220 |
| Gly-D-Phe-Tyr-NH$_2$ | 80/20 | 3.8 | 4.4 | 280 |
| Leu-encephaline amide | 80/20 | 6.1 | 7.6 | 220 |

*10 mM tetrabutylammonium sulfate/acetonitrile

In addition, the presence of possible protease- or peptidase activity was tested for with the aid of thin-layer chromatography. No release of amino acids could be detected for any of the peptides.

TABLE 4a

Conversion of dipeptide amides

| Substrate (10 mM) | Relative conversion (%) |
|---|---|
| Ala-Gly-NH$_2$ | 39 |
| Phe-Gly-NH$_2$ | 51 |
| Tyr-Gly-NH$_2$ | 54 |
| Leu-Gly-NH$_2$ | 54 |
| Gly-Gly-NH$_2$ | 8 |
| Val-Gly-NH$_2$ | 22 |
| Pro-Gly-NH$_2$ | 66 |
| Gly-Tyr-NH$_2$ | 174 |
| Phe-Ala-NH$_2$ | 203 |
| Ala-Ala-NH$_2$ | 211 |
| Leu-Ala-NH$_2$ | 217 |
| Gly-Phe-NH$_2$ | 214 |
| Tyr-Phe-NH$_2$ | 190 |
| Ser-Phe-NH$_2$ | 217 |
| Ala-Phe-NH$_2$ | 218 |
| Leu-Phe-NH$_2$ | 203 |
| Val-Phe-NH$_2$ | 140 |
| His-Phe-NH$_2$ | 137 |
| Pro-Phe-NH$_2$ | 158 |
| Tyr-Pro-NH$_2$ | 0 |
| Ala-Asn-OH | 0 |
| Gly-Asn-OH | 0 |
| Ala-Gln-OH | 0 |

TABLE 4b

Conversion of N-acetyl amino acid amides

| Substrate (10 mM) | Relative conversion (%) |
|---|---|
| Ac-Ala-NH$_2$ | 182 |
| Ac-Val-NH$_2$ | 1 |
| Ac-Ile-NH$_2$ | 6 |
| Ac-D,L-neopentylglycine amide | 131 |
| Ac-Pro-NH$_2$ | 0 |
| Ac-Cys-NH$_2$ | 82 |
| Ac-D,L-Met-NH$_2$ | 102 |
| Ac-Ser-NH$_2$ | 58 |
| Ac-Thr-NH$_2$ | 21 |
| Ac-Phe-NH$_2$ | 134 |
| Ac-Tyr-NH$_2$ | 123 |
| Ac-Phg-NH$_2$* | 28 |
| Ac-Trp-NH$_2$ | 157 |
| Ac-Nal-NH$_2$* | 84 |
| Ac-Lys-NH$_2$ | 175 |
| Ac-Arg-NH$_2$ | 110 |
| Ac-His-NH$_2$ | 177 |
| Ac-Glu-NH$_2$ | 162 |

*Phg = phenylglycine Nal = naphthylalanine

TABLE 4c

Influence of the protective group and of adjacent amino acid on the deamidation of the C terminus

| Substrate (10 mM) | Relative conversion (%) |
|---|---|
| Ac-Tyr-NH$_2$ | 123 |
| Bz-Tyr-NH$_2$ | 173 |
| Gly-Tyr-NH$_2$ | 174 |
| Phe-Ala-NH$_2$ | 203 |
| Ala-Ala-NH$_2$ | 211 |
| Leu-Ala-NH$_2$ | 217 |
| Z-Ala-NH$_2$ | 62 |
| Z-D-Ala-NH$_2$ | 0 |
| N-Methoxy-D,L-Met-NH$_2$ | 109 |
| N-Ethoxy-D,L-Met-NH$_2$ | 124 |
| N-Carbamoyl-D,L-Met-NH$_2$ | 77 |

TABLE 4c-continued

Influence of the protective group and of adjacent amino acid on the deamidation of the C terminus

| Substrate (10 mM) | Relative conversion (%) |
|---|---|
| N-Acetyl-D,L-Met-NH$_2$ | 102 |
| Arg-Met-NH$_2$ | 125 |

TABLE 4d

Enzymatic conversion of unprotected amino acid amides

| Substrate (10 mM) | Conversion |
|---|---|
| H-Ala-NH$_2$ | 0 |
| H-arg-NH$_2$ | 0 |
| H-Leu-NH$_2$ | 0 |
| H-Tyr-NH$_2$ | 0 |
| H-Met-NH$_2$ | 0 |
| H-Phe-NH$_2$ | 0 |
| H-Lys-NH$_2$ | 0 |
| H-Val-NH$_2$ | 0 |
| H-Ile-NH$_2$ | 0 |
| H-Thr-NH$_2$ | 0 |
| H-Trp-NH$_2$ | 0 |
| H-Ser-NH$_2$ | 0 |
| H-D-Ala-NH$_2$ | 0 |
| H-D-Leu-NH$_2$ | 0 |

TABLE 4e

Enzymatic conversion of longer-chain peptides

| Substrate (10 mM) | Relative conversion (%) |
|---|---|
| Z-Pro-Leu-Gly-NH$_2$ | 50 |
| Z-Gly-Gly-Leu-NH$_2$ | 6 |
| Gly-Phe-D-Phe-NH$_2$ | 0 |
| Gly-D-Phe-Tyr-NH$_2$ | 33 |
| Leu-encephaline amide | 52 |

The results show that with the exception of L-Pro, all proteinogenous, protected amino acid amides and peptide amides are deamidated. Even a few protected, non-proteinogenous amino acid amides are hydrolyzed (phenylglycine, naphthylalanine, neopentylglycine). D-amino acids in the C-terminal position are not converted. The amide function in the side chains of asparagine and glutamine are not attacked. The peptide bonds of longer-chain oligopeptides are not split, unprotected amino acid amides are not converted.

EXAMPLE 6

Splitting of Racemic Mixtures of N-protected Zmino Acid Amides

The tests for the splitting [separation] of racemic mixtures took place in 50 mM triethylammonium carbonate buffer, pH 7.5. The test batches a 50 ml with 20 U peptide amidase each were incubated at 30° C. Z-D,L-Ala-NH$_2$, Ac-D,L-Met-NH$_2$ and Ac-D,L-neopentylglycine amide (Ac-D,L-Npg-NH$_2$) were available as substrates. The concentration of the substrates in the reaction batch was 10 mM. Specimens were taken at different times, the reaction stopped by heating for 5 minutes at 95° C. and the enantiomeric purity examined with HPLC. The results are shown in the following:

| | |
|---|---|
| Z-D-Ala-OH | 0.4% |
| Z-L-Ala-OH | 99.6% |
| Ac-D-Met-OH | 0.2–0.3% |
| Ac-L-Met-OH | 99.7–99.8% |
| Ac-D-Npg-OH | 0.2% |
| Ac-L-Npg-OH | 99.8%. |

Figure 6:
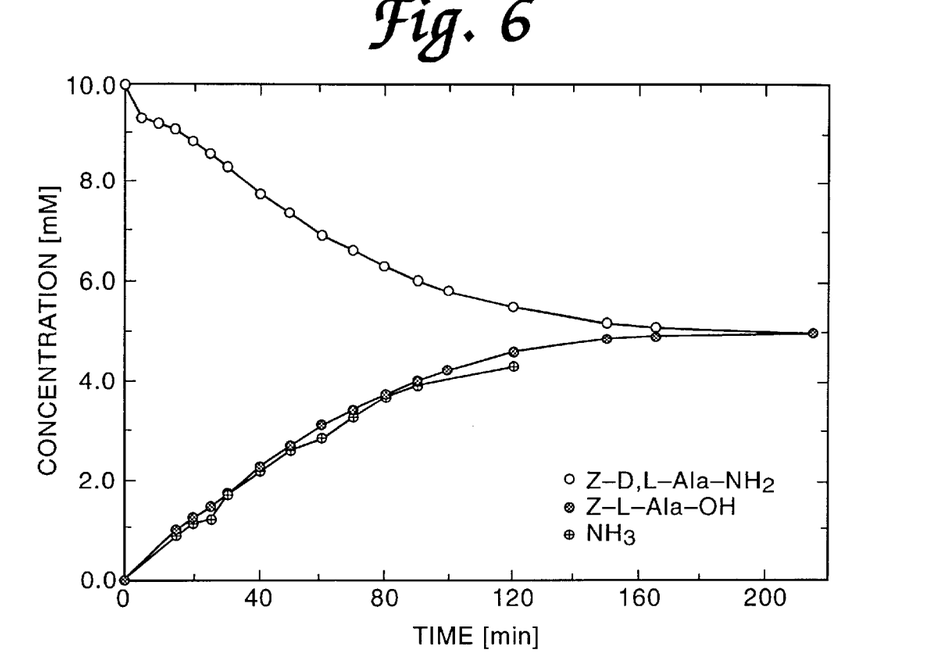
FIG. 6 shows the splitting [separation] of racemic mixtures of Z-D,L-Ala-$NH_2$ with the peptide amidase from *Xanthomonas maltophilia*.
Figure 7:
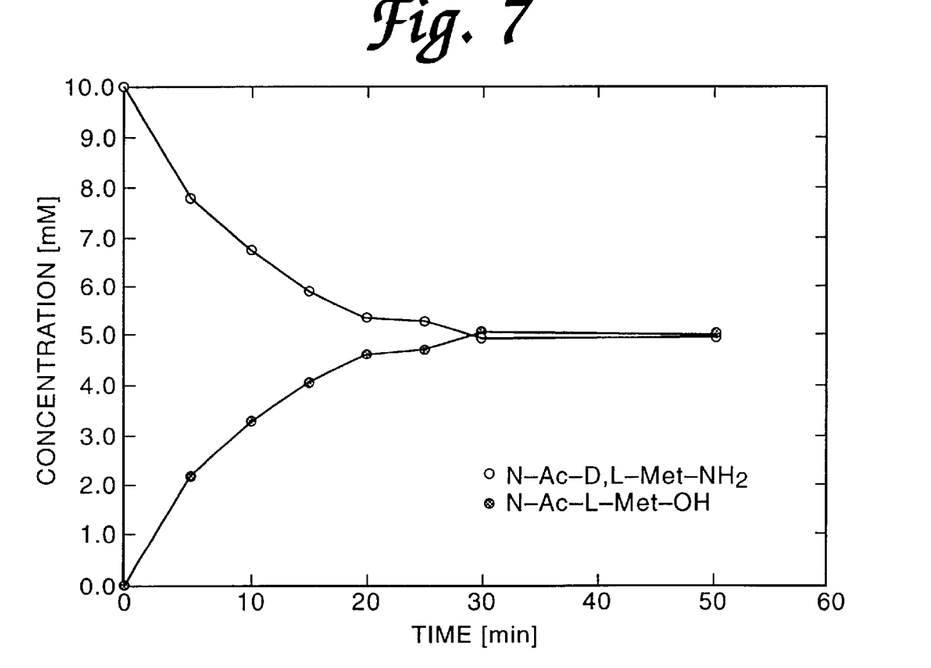
FIG. 7 shows the enantioselective deamidation of N-Ac-D,L-Met-$NH_2$ with the peptide amidase from *Xanthomonas maltophilia*.

The results are also shown in FIG. 6, which refers to the splitting of racemic mixtures of Z-D, L-Ala-$NH_2$, and FIG. 7, which shows the enantioselective deamidation of N-Ac-D,L-Met-$NH_2$.

EXAMPLE 7

Influence of Enzyme Effectors on the Peptide Amidase Activity

The tests took place in 50 mM tris/HCl, pH 7.5. After a preincubation of the enzyme (38 mU per batch, purification stage after the gel filtration) with the effector (10 mM in the test batch) for 1 h at 30° C. the reaction was started by adding substrate (Z-Gly-Tyr-$NH_2$, 10 mM in the test batch). The reaction batches were incubated for 2.5 h at 30° C. Table 5 shows the results of the influence of enzyme effectors on the peptide amidase activity. It is apparent that peptide amidase belongs neither to the classic serine hydrolases which are inhibited at a concentration of PMSF of 1 mM or of Pefabloc of 0.2 mM nor to the metalloenzymes which are inhibited by EDTA or 1.10-phenanthroline in the concentration range indicated here.

TABLE 5

Enzymatic activity in the presence of potential inhibitors

| Potential inhibitor (10 mM in the test) | residual activity (%) |
|---|---|
| $CuSO_4 * 5 H_2O$ | 103 |
| $CoCl_2 * 6 H_2O$ | 80 |
| $NiCl_2 * 6 H_2O$ | 93 |
| $HgCl_2 * 6 H_2O$ | 67 |
| EDTA | 96 |
| 1,10-phenanthroline | 92 |
| 2,2'-dipyridyl | 97 |
| D-cycloserine | 100 |
| Semicarbazide | 99 |
| 1,4-dithio-D,L-threitol (DDT) | 96 |
| Actinonine | 106 |
| Phenylmethane sulfonyl fluoride (PMSF) | 58 |
| 4-(2-aminoethyl)-benzylsulfonyl fluoride | |
| (Pefabloc) 10.0 mM | 0 |
| 0.3 mM | 62 |
| 0.1 Mm | 82 |

EXAMPLE 8

Figure 8:
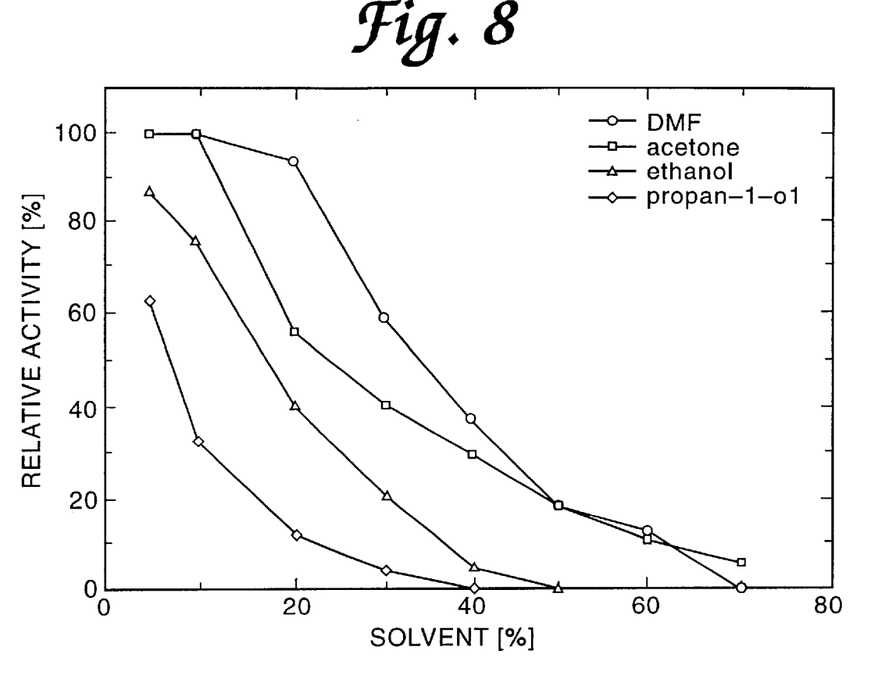
FIG. 8 shows the influence of solvent on the enzymatic activity of the peptide amidase from *Xanthomonas maltophilia*.

Influence of Solvents on the Peptide Amidase Activity and Stability of Peptide Amidase During Incubation in Solvent 200 µl enzyme solution (59 µg BSAeq/ml, purification stage after the gel filtration) were compounded in each instance with 700 µl of an appropriate mixture of 50 mM tris/solvent, pH 7.5 for the examinations of the influence of solvents on the peptide amidase activity. Dimethylformamide (DMF), acetone, ethanol and propan-1-ol, which were present in the reaction batch up to 70% by volumetric amount, were tested as solvents. The reaction was started by adding substrate Z-Gly-Tyr-$NH_2$. The incubation took place for 90 minutes at 30° C. Then, aliquots of 100 µl of the reaction batches were provided with 100 µl glacial acetic acid and the enzyme activity determined as described in 1.4. FIG. 8 shows the results of the influence of solvents on the enzyme activity. It is apparent that at 20% DMF, 94% residual activity is still present and even at 30%, 59% is still present. In the presence of other solvents such as propan-2-ol the enzyme distinctly loses activity but is nevertheless not completely inactivated at a content of 10% (residual activity 30%).

Figure 9:
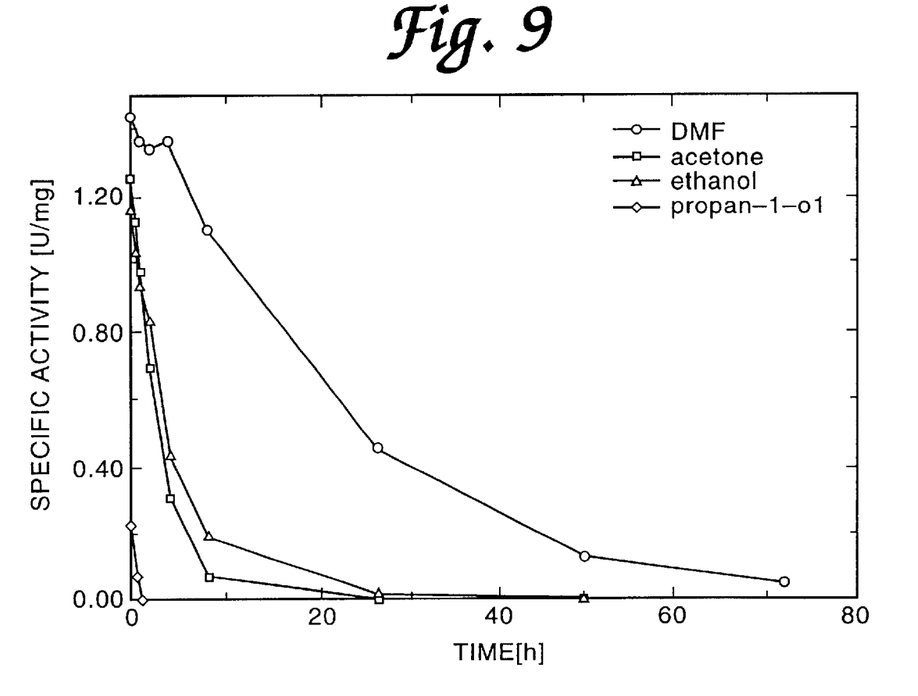
FIG. 9 shows the solvent stability of the peptide amidase from *Xanthomonas maltophilia*.

In order to determine the solvent stability of peptide amidase from Xanthomonas maltophilia, 600 µl enzyme solution à 57 µg BSAeq/ml (purification state after the gel filtration) was compounded with 150 µl solvent and, as control, 150 µl 50 mM tris/HCl, pH 7.5. The incubation took place at 30° C. Specimens for the determination of activity were drawn at different times. Dimethylformamide (DMF), acetone, ethanol and propan-1-ol were tested as solvent. FIG. 9 shows the solvent stability of peptide amidase from Xanthomonas maltophilia. After 26 hours, a residual activity of 32% still results at a solvent content of 20% DMF.

EXAMPLE 9

Determination of the Molar Mass

The relative molar mass of peptide amidase from Xanthomonas maltophilia was determined by gel filtration (travel conditions see 1.3.2). The following calibration proteins were used.

| | Molecular weight (daltons) | $V_e$ (ml) | $K_{AV}$ (–) |
|---|---|---|---|
| Ribonuclease A | 13700 | 85.6 | 0.53 |
| Chymotrypsinogen | 25000 | 77.9 | 0.42 |
| Ovalbumin | 43000 | 65.7 | 0.26 |
| Bovine serum albumin | 67000 | 58.6 | 0.16 |
| Blue dextran 2000 | 2000000 | 26.4 | 0.00 |

The detection took place at 280 nm. The elution volume of the peptide amidase was determined by determination of activity. The relative molar mass was determined from the elution volume, using the calibration curve, at 38000±1000 daltons.

EXAMPLE 10

Inducibility of Peptide Amidase from Xanthomonas Maltophilia 1 l Erlenmeyer flasks were provided with 200 ml of the nutrient medium used in the second part of the screening for the examinations of the inducibility of peptide amidase from Xanthomonas maltophilia. The amount of yeast extract was raised to 0.1% thereby and only one amide derivative added to 0.5% of the medium in each instance. In addition, media without the addition of amides and with 1.5% yeast extract were examined. Ac-DL-Met-$NH_2$, leucine amide and carnitine amide were used as amides. The flasks were inoculated to 0.5% and agitated 2 days at 30° C. and 120 rpm. The obtention of the raw extracts took place as already described above. Table 6 shows the results. It is apparent from the data that the enzyme is formed even without the addition of Ac-DL-Met-NH$_2$ as inductor in the cell, but that the specific activity can be doubled to tripled by the addition of this inductor. On the other hand, the addition of other amides shows no influence.

TABLE 6

Induction of peptide amidase from Xanthomonas maltophilia

| Additives | Activity (mU/ml) | Protein content (mg (BSAeq/ml) | Spec. activity (mU/mg BSAeq) |
|---|---|---|---|
| Without additive | 29 | 6.62 | 4 |
| 1.5 yeast extract | 58 | 8.29 | 7 |
| Ac-DL-Met-NH$_2$ | 88 | 6.65 | 13 |
| Leu-NH$_2$ | 15 | 5.22 | 3 |
| Carnitine amide | 30 | 7.13 | 7 |

EXAMPLE 11

Preparation of Racemic, N$_\alpha$-protected Amino Acid Amides for the Enzymatic Separation with Peptide Amidase A) N$_\alpha$-formyl-DL-methionine amide 30 g (0.20 mole) DL-methionine amide was agitated with 250 ml methyl formate for two days at room temperature, during which fine, slightly yellow crystals developed. They were filtered off and recrystallized out of a mixture of 150 ml hexane and 160 ml ethanol. After cooling off, filtering, washing and drying, 23 g (55%) N$_{60}$ -formyl-DL-methionine amide was obtained in the form of colorless crystals with a melting point of 121–122° C.

B) N$_{60}$ methylaminocarbonyl-DL-methionine Amide 18 ml (0.3 mole) methylisocyanate was dripped into a solution of 30 g (0.2 mole) DL-methionine amide in 350 ml water at 5–10° C., during which a colorless, crystalline precipitate formed. After 30 min of subsequent agitation at 5–10° C. and 30 min at room temperature, the crystals were filtered off, washed with water and dried, yielding 25 g product. A concentrating of the mother liquor yielded a further 10 g. 29 g (70%) N$_\alpha$methylaminocarbonyl-DL-methionine amide in the form of light, flaky crystals with a melting point of 156–157° C. were obtained by recrystallization out of methanol/acetic ester.

C) N$_\alpha$-methoxycarbonyl-DL-methionine Amide 85 ml (1.11 moles) methylchloroformate were dripped into a solution of 150 g (1.02 moles) DL-methionine amide in 200 ml water at 5–10° C., during which the pH was maintained at 8–10 by the addition of sodium hydroxide solution. After 30 min of subsequent reaction, 60 ml water was added, whereupon crystals formed which were filtered off, washed with water and dissolved in 250 ml water. This solution was extracted twice and the crystallization mother liquor extracted once with 500 ml methylene chloride in each instance. After drying in a vacuum, 162 g yellowish, crystalline residue remained. It was dissolved in 200 ml hot ethanol. Then, 400 ml MTBE was added and after the appearance of the first colorless crystals another 200 ml MTBE. After cooling in an ice bath, filtering off, washing with 200 ml MTBE and drying, 127 g (60k) N$_\alpha$-methoxycarbonyl-DL-methionine amide with a melting point of 93–94° C. was obtained.

D) N$_\alpha$-ethoxycarbonyl-DL-methionine amide 106 ml (1.10 moles) ethylchloroformate were dripped into a solution of 150 g (1.02 moles) DL-methionine amide in 200 ml water at 5–10° C., during which the pH was maintained at 7–9 by adding sodium hydroxide solution. A thick, finely crystalline precipitate rapidly formed. A suspension which was just able to still be agitated was obtained by the addition of 800 ml water, which suspension was agitated 3 hours further at room temperature. Then the colorless crystals were filtered off, washed with water and recrystallized out of 900 ml water. After cooling to 0–5° C., filtering off, washing with water and drying, 129 g (57%) N$_\alpha$ethoxycarbonyl-DL-methionine amide with a melting point of 110–112° C. was obtained.

E) N$_\alpha$-benzyloxycarbonyl-DL-methionine Amide 51 ml benzyloxycarbonyl chloride was dripped into a solution of 50 g (0.34 mole) DL-methionine amide in 200 ml water at 5–20° C., during which the pH was maintained at 7–9 with sodium hydroxide solution. A slimy precipitate formed immediately which became finely crystalline upon the addition of 200 ml MTBE. After the end of the addition the mixture was agitated 30 min further at room temperature. The precipitated, colorless crystals were then filtered off, washed with a little MTBE and recrystallized out of 700 ml toluene. After filtering off, washing with toluene and drying, 67 g (69%) N$_\alpha$benzyloxycarbonyl-DL-methionine amide with a melting point of 120–122° C. was obtained.

F) N$_\alpha$-acetyl-DL-neopentylglycine Amide 12 ml (0.13 mole) acetic anhydride was dripped into a solution of 17 g (0.12 mole) DL-neopentylglycine in 200 ml water under ice cooling in approximately 30 min, during which the pH was maintained at approximately 8 with sodium hydroxide solution. After 1 h agitation at room temperature, an extraction was performed three times with 100 ml methylene chloride and the organic phase was evaporated after drying over sodium sulfate. 20 g (89%) N-acetyl-DL-neopentylglycine remained as colorless solid.

Then, 14 ml (0.1 mole) triethylamine was dripped into 19 g (0.1 mole) N-acetyl-DL-neopentylglycine in 150 ml THF at −10° C. in 15 min. After 10 min a solution of 10 ml (0.1 mole) ethylchloroformate in 10 ml THF was added dropwise in such a manner that the temperature did not exceed −5° C. Then, 70 ml 25% ammonia solution were added all at once, then 50 ml THF, following which the mixture was agitated 2 h at −5° C. and overnight at room temperature. The batch was then evaporated to dryness, thoroughly agitated with 100 ml water, the solid filtered off and recrystallized out of 70 ml methanol. A total of 15 g (78%) N$_\alpha$-acetyl-DL-neopentylglycine amide was obtained in the form of colorless crystals with a melting point >205° C.

G) N$_\alpha$-benzyloxycarbonyl-DL-neopentylglycine amide 15 ml (0.11 mole) benzyloxycarbonylchloride was dripped into a solution of 15 g (0.10 ml) DL-neopentylglycine in 150 ml water under ice cooling in approximately 30 min, during which the pH was maintained at approximately 9 with sodium hydroxide solution. After 1 h agitation at room temperature an extraction was carried out three times with 75 ml methylene chloride and the organic phase dried in a rotary vacuum after drying over sodium sulfate. 25 g (90t) N-benzyloxycarbonyl-DL-neopentylglycine remained as a colorless oil which crystallized upon standing.

Then, 12 ml (0.90 mole) triethylamine was dripped into 24 g (0.09 mole) N-benzyloxycarbonyl-DL-neopentylglycine in 150 ml THF at −10° C. in 15 min. After 10 min a solution of 8 ml (0.09 mole) ethylchloroformate in 10 ml THF was added dropwise in approximately 30 min in such a manner that the temperature did not exceed −5° C. After 30 min agitation at −5° C., 60 ml 25% ammonia solution were added all at once and the mixture then agitated 2 h at −5° C and overnight at room temperature. The batch was then evaporated to dryness, taken up with 50 ml water and extracted with 150 ml methylene chloride. After drying of the organic phase over sodium sulfate and drying in a rotary vacuum, 26 g residue remained which was dissolved in 50 ml methanol and then compounded with 70 ml water within approximately 2 h under ice cooling. After filtration, washing with methanol/water and drying, 13 g (54%) $N_\alpha$benzyloxycarbonyl-DL-neopentylglycine amide were obtained as a colorless solid with a melting range of 132–137° C.

EXAMPLE 12

Preparation of D-neopentylglycine from N-acetyl-D,L-neopentylglycine Amide 10 mM N-acetyl-D,L-neopentylglycine amide were incubated with 20 U peptide amidase in a 50 ml Erlenmeyer flask in 50 mM triethylammonium carbonate buffer at pH 7.5 and 30° C. The conversion was controlled by HPLC. After 24 hours the conversion was 50% and did not change any more as time passed. The enzyme was now deactivated by five minutes of heating and the enantiomeric purity examined. The purity of N-acetyl-L-neopentylglycine (determined by ligand exchange chromatography) was 99.8% and the purity of the N-acetyl-D-neopentylglycine amide (determined by inclusion chromatography) was 99.7%. The two products were separated by anion exchange chromatography on Amberlite M 500 and the N-acetyl-D-neopentylglycine amide converted by several hours of hydrolysis in 6-normal, boiling hydrochloric acid into the free D-amino acid, during which the demonstration of the complete conversion by HPLC or DC takes place. The amount of rotation of the D-neopentylglycine $[\alpha^{25}_D]$ (c=0.5, 6N HCl) was −16.2°.
Methods Used for the Separation of Enantiomers The enantiomers of the remaining N-acyl-amino acid amide were separated from each other by inclusion chromatography and the two enantiomers of the N-acyl amino acid product by ligand exchange chromatography.

What is claimed is:
1. A process for the enzymatic cleavage of a C-terminal amino group from a peptide amide or from an N-terminally protected amino acid amide to form a peptide or N-terminally protected amino acid, said process comprising deamidating said peptide amide or N-terminally protected amino acid amide with a microbial peptide amidase, wherein said microbial peptide amidase:
   (a) selectively and hydrolytically splits off the free amino group on the C-terminal end of peptide amides;
   (b) does not split peptide bonds;
   (c) does not deamidate N-substituted amino acid amides;
   (d) has an optimum pH of 6.0±0.5;
   (e) is obtained by the process of cultivating *Xanthomonas maltophilia* microorganisms containing peptide amidase in nutrient media comprising a source for carbon, nitrogen and mineral salts, said process comprising the steps of:
      (i) incubating said microorganisms in a first nutrient medium containing amide nitrogen as a nitrogen source to produce colonies;
      (ii) inoculating said colonies onto a second nutrient medium containing N-acetyl-D,1-methionine amide; and
      (iii) incubating said colonies so that microorganisms which grow in both nutrient media are selected; and
   and wherein said peptide amidase has the N-terminal amino acid sequence of SEQ ID NO:1.
2. Process of claim 1, wherein said peptide amidase is obtained from the microorganism *Xanthomonas maltophilia*, deposited with the German Collection for Microorganisms under No. DSM 9181.
3. The process of claim 1, wherein said peptide amidase:
   (a) is stable in the pH range between pH 7 and pH 8;
   (b) has an optimum temperature of about 40° C. at a pH of 7.5;
   (c) is inhibited at serine groups by phenylmethane sulfonylfluoride and 4-(2-aminoethylbenzylsulfonylfluoride);
   (d) has a molecular weight as determined by gel filtration of approximately 38,000 daltons;

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 17 amino acids
      (B) TYPE: amino acid
      (C) STRANDEDNESS: single
      (D) TOPOLOGY: linear    (ii) MOLECULE TYPE: peptide    (xi) SEQUENCE DESCRIPTION: SEQ ID NO: 1:

```
Xaa Arg Asn Val Pro Phe Pro Tyr Ala Glu Thr Asp Val Ala Asp
1               5                   10                  15

Leu Gln
```

(e) has an isoelectric point of approximately pH 5.8; and (f) has isozymic forms having all of the identifying characteristics of said peptide amidase.

4. The process of any one of claims 1–3, wherein the deamidation reaction is carried out in a continuous manner.

5. The process of any one of claims 1–3, wherein the deamidation reaction is carried out in a continuous manner; the peptide amide is enzymatically hydrolyzed by the peptide amidase to yield the peptide; and the peptide is separated from the reaction mixture on the basis of its charge to obtain the amino acid amide.

* * * * *